(12) United States Patent
Brunner et al.

(10) Patent No.: US 7,786,303 B2
(45) Date of Patent: Aug. 31, 2010

(54) ACIDIC BATH FOR ELECTROLYTICALLY DEPOSITING A COPPER DEPOSIT CONTAINING HALOGENATED OR PSEUDOHALOGENATED MONOMERIC PHENAZINIUM COMPOUNDS

(75) Inventors: Heiko Brunner, Mannheim (DE);
Wolfgang Dahms, Berlin (DE); Udo Grieser, Berlin (DE); Olanda Grieser, legal representative, Berlin (DE);
Christopher Grieser, legal representative, Berlin (DE)

(73) Assignee: Atotech Deutschland GmbH, Berlin (DE)

( * ) Notice: Subject to any disclaimer, the term of this patent is extended or adjusted under 35 U.S.C. 154(b) by 1016 days.

(21) Appl. No.: 10/575,304

(22) PCT Filed: Nov. 9, 2004

(86) PCT No.: PCT/EP2004/012851
§ 371 (c)(1),
(2), (4) Date: Apr. 11, 2006

(87) PCT Pub. No.: WO2005/049584
PCT Pub. Date: Jun. 2, 2005

(65) Prior Publication Data
US 2007/0108062 A1    May 17, 2007

(30) Foreign Application Priority Data
Nov. 19, 2003    (DE) ................................ 103 54 860

(51) Int. Cl.
*C07D 241/26* (2006.01)
(52) U.S. Cl. .................................... 544/348
(58) Field of Classification Search .................. 544/348
See application file for complete search history.

(56) References Cited
U.S. PATENT DOCUMENTS
2,707,166 A   4/1955  Brown et al.
3,267,010 A   8/1966  Creutz et al.
3,743,584 A   7/1973  Todt et al.
6,425,996 B1 *  7/2002  Dahms et al. ............... 205/298

FOREIGN PATENT DOCUMENTS
DE    947 656    8/1956
DE    1 521 062    4/1963
DE    2 028 803    6/1970
JP    60-056086    1/1985

OTHER PUBLICATIONS

Dörwald, F. Zaragoza. Side Reactions in Organic Synthesis: A Guide to Successful Synthesis Design, Weinheim: Wiley-VCH Verlag GmbH & Co. KGaA, 2005, Preface.*
1973:43420 CAPLUS relating to A. Ya. Il'chenco and V.N. Rudenko in:Khimiya Geterotsiklicheskikh Soedineii (1972), (10), 1425-1429 schematically discloses the synthesis of 3-chlro-5-methyl-7-(phenylamino)-phenazinium perchlorate.
Kerhmann F et al: "Zur Kenntniss der Fluoridine" Chemische Berichte, vol. 34, 1901, pp. 1217-1224, XP002319720.
Kehrmann F: "Neue Synthesen in der Gruppe der Chinonimid-Farbstoffe, III: Synthesen der Induline 3B und 6B" Chemische Berichte, vol. 56, No. 11, Dec. 5, 1923, pp. 2394-2397, XP002319719.
Balls K et al: "Studies in the azine series. Part II" Journal of the Chemical Society, vol. 101, No. 2, 1912, pp. 1840-1852, XP008043856.

* cited by examiner

*Primary Examiner*—James O Wilson
*Assistant Examiner*—Douglas M Willis
(74) *Attorney, Agent, or Firm*—Frank J. Bonini, Jr.; John F. A. Earley, III; Harding, Earley, Follmer & Frailey, P.C.

(57) ABSTRACT

For manufacturing particularly uniform and mirror bright copper coatings that are leveled and ductile as well using a relatively high current density, halogenated or pseudohalogenated monomeric pheanzinium compounds or a purity at least 85 mole-% and having the general chemical formula (I) are utilized in which $R^1$, $R^2$, $R^3$, $R^4$, $R^7$, $R^{7''}$, $R^8$, $R^9$, X and A have the significations denoted in the claims. The compounds are prepared by diazotizing a suited starting compound prior to halogenating or pseudohalogenating it in the presence of mineral acid, diazotization means and halide or pseudohalide, with the reaction steps being run in one single vessel.

12 Claims, No Drawings

ACIDIC BATH FOR ELECTROLYTICALLY DEPOSITING A COPPER DEPOSIT CONTAINING HALOGENATED OR PSEUDOHALOGENATED MONOMERIC PHENAZINIUM COMPOUNDS

BACKGROUND OF THE INVENTION

1. Field of the Invention

The invention relates to halogenated or pseudohalogenated monomeric phenazinium compounds, to a method of preparing same, to an acidic bath containing said compounds for electrolytically depositing a copper deposit as well as to a method of electrolytically depositing a copper deposit using said acidic bath. The halogenated or pseudohalogenated monomeric phenazinium compounds may be used as additives in copper plating baths to more specifically form mirror bright level deposits of copper in order to produce decorative surfaces. The compounds may moreover be used as additives in copper plating baths to selectively and completely fill with copper blind microvias in printed, circuit boards and trenches and vias on semiconductor, wafers. The compounds may also be utilized as additives in copper plating baths for depositing copper onto semiconductor substrate surfaces provided with recesses during the manufacturing process of integrated circuits, with the entire semiconductor substrate surface being uniformly coated with copper.

2. Brief Description of the Related Art

For depositing bright copper surfaces, organic additives are usually added in small quantities to most of the acidic copper electrolytes in order to obtain bright copper layers instead of a crystalline matte deposit. In this approach, an additive compound or a combination of several additive compounds such as polyethylene glycols, thioureas and the derivatives thereof, thio hydantoin, thio carbamic acid esters as well as thio phosphoric acid esters is often added. Nowadays however, the additives mentioned are no longer significant, due to the fact that the quality of the thus obtained copper layers meets by no means today's requirements. The thus obtained coatings are either too brittle or exhibit poor brightness and insufficient leveling.

The utilization of certain phenazinium compounds such as phenazine dyestuffs e.g., safranines and of the derivatives thereof, that are also used as paper and leather dyes and as dyes for keratin-containing fibers, has long been known for producing bright copper layers. In accordance with DE-PS 947 656, these dyes, e.g., dimethyl safranine azo dimethyl aniline, diethyl safranine azo dimethyl aniline, Janus grey and safranine azo naphthol are being used as the only additives. It is moreover known to use said compounds in combination with other additives as well.

Further, DE-AS 1 521 062 suggests bath compositions containing an organic sulfide that contains at least one sulfonic acid group as well as, mixed thereto or chemically bonded, a polyether that contains at least three, preferably six, oxygen atoms and is free of aliphatic hydrocarbon chains having more than six C-atoms. These baths permit deposition of smooth, bright and ductile copper layers. Preferred polyethers mentioned are 1,3-dioxolane polymerisates having a molecular weight of at least 296, preferably of about 5000. Phenazine dyestuffs may also be utilized in combination with the bath additives mentioned, for example diethyl phenosafranine azo dimethyl aniline, dimethyl phenosafranine azo dimethyl aniline, diethyl phenosafranine azo phenol and dimethyl azo-(2-hydroxy-4-ethylamino-5-methyl)-benzene. The phenazine dyestuffs permit high leveling and a wide range of bright deposits.

With the copper electrolytes described in DE-AS 1 521 062 however it is not possible to utilize a higher cathodic current density. Moreover, the deposited copper surfaces can only be nickel-plated after having been subjected to a preliminary intermediate treatment.

It is further known to use hydroxylated and halogenated phenazine dyestuffs of the safranine type as-levelers and brighteners, such as DE-OS 2 028 803. This document relates to polymeric phenazinium compounds, the phenazinium skeletale structure being substituted with hydrogen, lower alkyl or substituted or unsubstituted aryl.

1973:43420 CAPLUS relating to A. Ya. Il'chenko and V. N. Rudenko in: Khimiya Geterotsiklicheskikh Soedinenii (1972), (10), 1425-1429 schematically discloses the synthesis of 3-chloro-5-methyl-7-(phenylamino)-phenazinium perchlorate.

The use and production of monomeric halogenated phenazine dyestuffs for acidic copper baths is i.a. described In the Patent Abstracts of Japan corresponding to JP 60-056086 A. The dyestuffs are prepared in a two-stage synthesis consisting of a diazotization reaction and of a halogenation reaction. For diazotization, the corresponding safranine dyestuff is first dissolved in the heat and filtered. At a temperature of 0 to 5° C., it is then diazotized with sodium nitrite and later hydrochloric acid being added before it is finally heated. Once it has cooled down, the reaction solution is reacted at room temperature over a period of 10 hours in the presence of copper (II) chloride solution, copper powder and hydrochloric acid to form the chlorinated phenazine dyestuff. It describes, by way of example, the preparation of 7-diethylamino-3-hydroxy-5-phenyl-phenazinium sulfate, of a mixture of 3-chloro-7-diethylamino-5-phenyl-phenazinium chloride and 7-diethylamino-3-hydroxy-5-phenyl-phenazinium chloride and of 3,7-dichloro-2,8-dimethyl-5-phenyl-phenazinium chloride.

The disadvantage of the method described is that for each synthesis step, inclusive of the dissolution of the dyestuff, a separate reaction vessel is needed. As a result of the long reaction times and of the moderate stability of the diazonium compounds, which easily decompose in an acidic medium, uncontrolled reactions may take place, resulting in variable quality of the products desired. Moreover, such type of time-consuming reactions is very expensive from an economical point of view.

SUMMARY OF THE INVENTION

In order to avoid the above disadvantages of known copper baths, the object of the present invention is to more specifically provide additives by means of which particularly uniform and brilliant, meaning mirror bright, as well as leveled and ductile copper coatings may be reproducibly prepared. The additives are hereby intended to be readily synthesizable at a low cost while remaining unchanged in quality and exhibiting high purity. It further intends to enable production of mirror bright, leveled and ductile copper layers using a relatively high current density. The composition of such a copper plating bath is intended to constantly permit, during bath operation over a long period of time, to obtain copper layers having the required quality.

The present invention comprises providing halogenated or pseudohalogenated monomeric phenazinium compounds, the method of preparing said compounds, the acidic bath containing said compounds for electrolytically depositing a copper deposit, the uses of the bath, as well as the method of electrolytically depositing a copper deposit using the acidic bath containing said compounds.

The halogenated or pseudohalogenated monomeric phenazinium compounds of the invention can advantageously be used in a bath for electrolytically producing a mirror bright, leveled copper deposit for the purpose of forming decorative surfaces. The bath may for example be utilized for the decorative copper plating of plastic parts in the sanitary and automotive industry. Further, the compounds may also be advantageously used in a copper plating bath for electrolytically depositing a copper deposit onto printed circuit boards with said copper deposit selectively and completely filling blind microvias in the printed circuit boards. Moreover, the compounds may also be advantageously utilized in a copper plating bath for electrolytically depositing a copper deposit onto semiconductor substrate (wafer) surfaces provided with recesses during the manufacturing process of integrated circuits, more specifically onto surfaces having high aspect ratio recesses. The copper deposit is thereby uniformly produced on the entire semiconductor substrate surface.

DETAILED DESCRIPTION OF THE PREFERRED EMBODIMENTS

The compounds of the invention are meant to be halogenated or pseudohalogenated monomeric phenazinium compounds of a purity of at least 85 mole-%, preferably of at least 90 mole-%, with a purity of at least 95 mole-% being particularly preferred and a purity of at least 98 mole-% being most preferred, having the following general chemical formula:

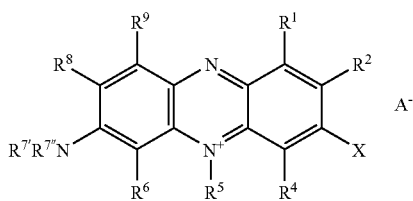

I wherein $R^1$, $R^2$, $R^4$, $R^6$, $R^{7'}$, $R^{7''}$, $R^8$ and $R^9$ are selected independently of each other from a group comprising hydrogen, halogen, amino, aminoalkyl, hydroxy, cyano, thiocyanate, isothiocyanate, cyanate, isocyanate, mercapto, carboxy (COO$^-$), the salt thereof, carboxylate ester (COOR), sulfo (SO$_3^-$), the salt thereof, sulfonate ester (SO$_3$R), lower alkyl, unsubstituted aryl, substituted aryl, heteroaryl and alicyclic heteroradicals, $R^5$ is selected from a group comprising lower alkyl, unsubstituted aryl, substituted aryl and heteroaryl, X is a halogen or a pseudohalogen and A$^-$ is an acid anion.

The phenazinium compounds of a purity of x mole-% as mentioned herein above, herein after and in the claims refer to a mixture of the phenazinium compounds and impurities, with the phenazinium compounds being contained in the mixture at a concentration of x mole-% and the impurities at a concentration of 100-x mole-%.

The term lower alkyl as mentioned herein above and herein after and in the claims preferably refers to $C_1$- to $C_4$-alkyl, meaning to methyl, ethyl, n-propyl, iso-propyl, n-butyl, iso-butyl and tert-butyl. By substituted alkyl as mentioned herein above, herein after and in the claims, sulfo- or carbonic acid-substituted alkyl is preferably meant.

Aryl as mentioned herein above or herein after and in the claims preferably refers to phenyl or polycyclic aromates such as naphthyl-1 and naphthyl-2, wherein these residues may be unsubstituted or substituted respectively. If these residues are substituted, they are more specifically substituted by alkyl, preferably by lower alkyl, halogen, hydroxy, amino, wherein amino is NH$_2$, NHR or NR'R", wherein R, R' and R" in turn can be lower alkyl, cyano, thiocyanate and mercapto. Phenyl may more specifically be substituted at a 2-, 4- and 6-position.

Heteroaryl as mentioned herein above or herein after and in the claims preferably refers to pyridinyl, quinolinyl and isoquinolinyl.

Alicyclic heteroradicals as mentioned herein above or herein after and in the claims more specifically refer to piperidyl, piperazinyl and morpholinyl.

Carbonic acid esters (COO esters) and sulfoester (SO$_3$ esters) as mentioned herein above or herein after and in the claims preferably refer to carbonic acid esters of the lower alcohols such as —COOCH$_3$, —COOC$_2$H$_5$ and so on or to sulfonic acid esters of the lower alcohols such as —SO$_3$CH$_3$, —SO$_3$C$_2$H$_5$ and so on, respectively. By lower alcohols $C_1$- to $C_4$-alcohols i.e., methanol, ethanol, n-propanol, iso-propanol, n-butanol, iso-butanol and tert-butanol are meant. —COO salts and —SO$_3$ salts as mentioned herein after refer to carbonic acid salts and sulfonic acid salts respectively, meaning more specifically the alkali salts, earth alkali salts, aluminium salts and copper salts such as —COO$^-$Na$^+$ or (—SO$_3$)$_2^-$Cu$^{2+}$.

Halogen as mentioned herein above or herein after and in the claims, more specifically in combination with the terms "hydrogen halide", "metal halide" and "halide", refers to fluorine, chlorine, bromine and iodine, preferably to chlorine and bromine.

Pseudohalogen and pseudohalide respectively as mentioned herein above or herein after and in the claims, refer to cyanate (—OCN), thiocyanate (—SCN), isocyanate (—NCO) and isothiocyanate (—NCS).

Alkali metal or earth alkali metal as mentioned herein above or herein after and in the claims, for example in "salt of earth alkali metal", preferably refers to sodium, potassium, magnesium and calcium.

In the phenazinium compounds of the invention, $R^1$, $R^2$, $R^4$, $R^6$, $R^{7'}$, $R^{7''}$, $R^8$ and $R^9$ are selected independently of each other from a group comprising hydrogen and lower alkyl. Alkyl may more specifically be methyl or ethyl.

Further in the phenazinium compounds of the invention, $R^5$ may preferably be aryl, more specifically phenyl.

In the compounds of the invention, X preferably is chlorine, bromine or thiocyanate.

Particularly suited phenazinium compounds are selected from a group comprising halogenated phenazinium compounds, the compounds herein below being the most preferred halogenated phenazinium compounds:

i) 3-chloro-7-N,N-dimethylamino-2-methyl-5-phenyl-phenazinium salt, more specifically the chloride:

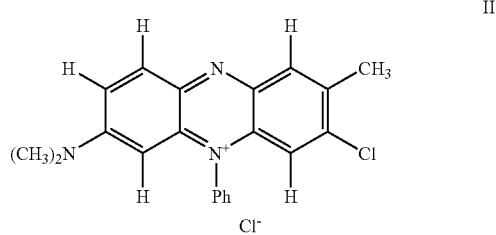

II ii) 3-bromo-7-N,N-dimethylamino-2-methyl-5-phenyl-phenazinium salt, more specifically the bromide: and

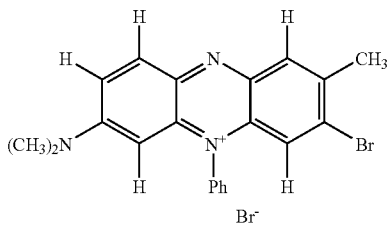

III iii) 3-bromo-7-N,N-diethylamino-5-phenyl-phenazinium salt, more specifically the bromide: as well as pseudohalogenated phenazinium compounds, the compound herein below being the most preferred pseudohalogenated phenazinium compound:

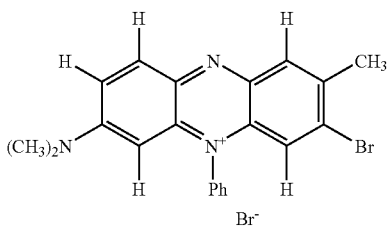

IV iv) 7-amino-2,8-dimethyl-3-thiocyanato-5-phenyl-phenazinium salt, more specifically the tetrafluoroborate:

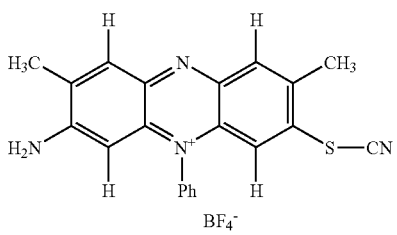

V

The compounds herein above are advantageously utilizable in an acidic copper-plating electrolyte. It has been found that the halogenated or pseudohalogenated monomeric phenazinium compounds are particularly advantageous in copper-plating baths, where they are characterized by a high plating activity.

Using the halogenated and pseudohalogenated monomeric phenazinium compounds of the invention in an acidic electrolytic copper-plating bath, it is possible to operate the latter at a high current density. In combination with well known other additives, it is moreover possible to achieve particularly even, brilliant copper deposits. Further, the efficiency of the halogenated and pseudohalogenated monomeric phenazinium dyestuffs is increased by the way they are synthesized in accordance with the invention as a result of the higher purity thereof. This purity amounts to at least 85 mole-%. This means that the substances of the invention contain a maximum of 15 mole-% of impurities. These impurities may more specifically be oligomers of the phenazinium compounds, for example the dimers and trimers thereof. In adding the compounds of the invention to a copper electrolyte, one accordingly achieves perfect brilliance although the concentration of additives used is clearly lower than when using comparable known phenazinium compounds of much lower purity. Efficiency and, as a result thereof, profitability are thus considerably increased.

In contrast to the phenazinium compounds of very high purity of the invention, the compounds described in Patent Abstracts corresponding to JP 60-056086 A are of much lower purity. These substances contain a considerable fraction of oligomers of phenazinium compounds, more specifically of dimers and trimers, as can be easily experimentally proven. This fraction of impurities typically lies within the range of 40 to 50 mole-%. Accordingly, the compounds disclosed in this document are much less suited for use as additives in an electrolytic copper-plating bath than the compounds of the invention.

The halogenated monomeric phenazinium compounds set forth below:
 i) 3-chloro-7-N,N-dimethylamino-2-methyl-5-phenyl-phenazinium salt,
 ii) 3-bromo-7-N,N-dimethylamino-2-methyl-5-phenyl-phenazinium salt,
 iii) 3-bromo-7-N,N-diethylamino-5-phenyl-phenazinium salt, and the pseudohalogenated monomeric phenazinium compounds, preferably:
 iv) 7-amino-2,8-dimethyl-3-thiocyanato-5-phenyl-phenazinium salt, have proved to be particularly efficient both separately and as a mixture, since they exhibit perfect brilliance both at a high and at a low current density with a much lower operative concentration being utilized in the copper electrolyte. These properties are already achieved using all of the phenazinium compounds of the invention, although to a different extent.

The reason for the higher purity of the compounds of the invention over the phenazinium compounds disclosed in the document mentioned herein above is due to the differing methods of preparation:

Due to the two-step preparation method in several synthesis vessels (diazotization and subsequent halogenation), the preparation of halogenated monomeric compounds in accordance with JP 60-056086 A is very complicated and time-consuming, with the quality and proportion of the desired products moreover varying as a result of the low stability of the diazonium compounds with respect to the long reaction time and this in turn may result in varying efficacy of said products or product mixtures in the electrolyte.

JP 60-056086 A neither describes nor mentions the preparation of pseudohalogenated monomeric phenazinium compounds.

Starting from monomeric phenazinium compounds of the general chemical formula VI given herein below, halogenated or pseudohalogenated monomeric phenazinium compounds, such as for acidic copper-plating baths, may now be selectively provided, with compounds of high purity being achievable in good yield:

The halogenated or pseudohalogenated monomeric phenazinium compounds are synthesized using a novel preparation method. In contrast to a conventional method in which, in a first synthesis step, a diazonium compound is formed from a monomeric phenazinium compound by diazotization in a first synthesis vessel in the presence of mineral acid and diazotization means, said diazonium compound being next reacted, in a second synthesis step and only after having been transferred to a second synthesis vessel, into a halogenated or pseudohalogenated monomeric phenazinium compound in the presence of mineral acid and copper(I) halide or pseudohalide, the method in accordance with the invention involves a first and a second reaction step that are both run in one single vessel in the presence of the monomeric phenazinium compound, the mineral acid, the diazotization means and the halide or pseudohalide (one pot method).

Thus, diazonium compounds are first formed using the one pot method, said diazonium compounds reacting immediately in situ in accordance with the invention to form the halogenated or pseudohalogenated monomeric phenazinium compounds. In the event of halogenation, if the mineral acid already contains halogen, further halides need not be added.

The reactions are thereby preferably run using a sufficiently high concentration of halides or pseudohalides, whereby said halides or pseudohalides may be supplied in the form of salts or acids. In order to obtain pure halogenated or pseudohalogenated monomeric phenazinium compounds in good yield, the halides or pseudohalides must be utilized, depending of the type, in molar excess over the phenazinium compounds. If the halides or pseudohalides are added in the form of metal halides, at least a onefold, preferably a twofold to threefold molar excess is needed. If hydrogen halides are the only halogen source used, an at least half-concentrated, preferably a concentrated acid is utilized in order to achieve a sufficiently high concentration of halide without addition of metal halides; an at least threefold molar excess over the phenazinium compounds is thereby required. The diazotization means is added to the one pot method preferably last or together with the halide or pseudohalide. The reaction temperature chosen is above room temperature, and preferably ranges from 30 to 70° C., the reaction time preferably ranging from one to three hours. Usually, the reactions are run at normal pressure although it is also possible to work at a pressure above atmospheric.

The monomeric phenazinium compounds which are preferably utilized as the starting compounds in the preparation method of the invention are meant to include in particular phenazinium compounds containing at least one primary amino group with phenazinium compounds of the general chemical formula VI being particularly preferred:

$R^{11}$ being each independently of each other hydrogen or lower alkyl. Alkyl preferably is methyl or ethyl.

Aminoalkyl is meant to preferably refer to N-methylamine, N-ethylamine, N,N-dimethylamine and N,N-diethylamine. Aryl can preferably be phenyl or tolyl.

The acid anion $A^-$ preferably is a sulfate, hydrogen sulfate, halide, more specifically chloride and bromide, tetrafluoroborate, hexafluorophosphate, nitrate, acetate, trifluoracetate or methanesulfonate.

The mineral acids used in the method of the invention are preferably selected from a group comprising hydrogen halides, sulfuric acid, tetrafluoroboric acid, hexafluorophosphoric acid, phosphoric acid and the mixtures thereof with the proviso that no hydrogen halide is used in the presence of the pseudohalides.

The preferably used diazotization means is metal nitrite, with sodium nitrite or nitrosylsulfuric acid being particularly preferred.

The halides used may for example be added in the form of a hydrogen halide and/or in the form of a metal halide, meaning in the form of a salt. The metal halides used are meant to preferably include transition metal halides such as copper, nickel and iron halides. According to these definitions, the following halides may for example be used: hydrochloric acid, hydrobromic acid, copper(I) chloride, copper(II) chloride, copper(I) bromide and nickel(II) chloride.

The pseudohalides used are preferably selected from a group comprising cyanate (—OCN), thiocyanate (—SCN), isocyanate (—NCO) and isothiocyanate (—NCS) and can be added in the form of alkali and/or earth alkali salts.

To prepare the halogenated monomeric phenazinium compound, the monomeric phenazinium compound may for example be suspended in the mineral acid and this suspension may then be heated, with stirring, to a temperature above room temperature, more specifically ranging for example from 30 to 70° C. Next, the halide, for example a metal halide dissolved in an aqueous solution, can be added. After having added the halide, the diazotization means, for example a saturated aqueous sodium nitrite solution, is added, prefer-

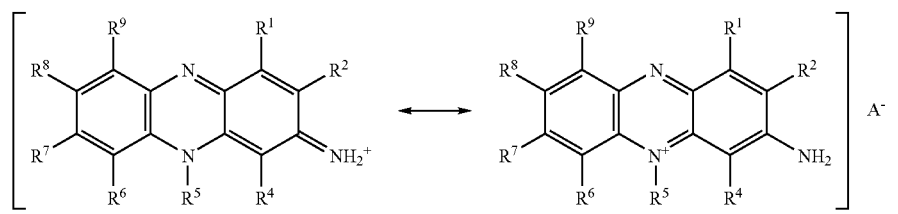

VI wherein $R^1$, $R^2$, $R^4$, $R^6$, $R^7$, $R^8$ and $R^9$ are selected independently of each other from the group comprising hydrogen, halogen, amino, amino alkyl, hydroxy, cyano, thiocyanate, isothiocyanate, cyanate, isocyanate, mercapto, carboxy, the salt thereof, carbonic ester, sulfo, the salt thereof, sulfo ester, lower alkyl, aryl, heteroaryl and alicyclic heteroradicals, $R^5$ is selected from a group comprising lower alkyl, aryl and heteroaryl, $A^-$ is an acid anion.

Particularly preferred monomeric phenazinium compounds of the general chemical formula VI are those belonging to the safranine dyestuffs, wherein $R^1$, $R^4$, $R^6$ and $R^9$ are each hydrogen, $R^5$ is phenyl and $R^7$ is $NR^{10}R^{11}$, with $R^{10}$ and ably with stirring. Alternatively, the halide and the diazotization means may also be added simultaneously, for example in a common solution.

In a preferred embodiment of the preparation method, the monomeric phenazinium compound can be suspended directly in a hydrogen halide, preferably at a high concentration. As a result thereof, there is no need for adding further halides. This embodiment differs more specifically from the known reaction scheme for halogenating diazonium compounds according to Sandmeyer in which this reaction step normally proceeds via a radical mechanism, as also described in JP 60-056086 A, with only a catalyst such as copper powder, copper(I) or copper(II) chloride participating in the reaction. By suspending said compound, as the only halide addition, in the respective hydrogen halide the method of the invention becomes faster, cheaper, with less impact on the environment.

In another preferred embodiment, the preparation of the halogenated monomeric phenazinium compound also advantageously departs from the Sandmeyer reaction scheme whereby here a nickel halide, for example nickel(II) chloride can be utilized instead of the known copper-type catalyst. This way of proceeding has not been described heretobefore in this context and results in significantly higher yields than achieved by conventionally utilizing copper(I) chloride.

For preparing the pseudohalogenated monomeric phenazinium compound, the monomeric phenazinium compound may again be suspended preferably in the mineral acid and then heated, with stirring, to a temperature above room temperature, more specifically ranging for example from 30 to 70° C. Next, the pseudohalide, for example a metal pseudohalide dissolved in an aqueous solution, may be added. After or during addition, for example in a common solution with the pseudohalide, the diazotization means, for example nitrosylsulfuric acid, may be added with stirring.

After the respective one of the reactions ends, the resulting halogenated or pseudohalogenated monomeric phenazinium compounds can be isolated frond the reaction formulation by adding acid-neutralizing agents.

The acid-neutralizing agents preferably include earth alkali and alkali metal hydroxides, more specifically caustic soda or caustic potash lye, magnesium and calcium oxide, earth alkali and alkali metal carbonates and phosphates, more specifically sodium or magnesium carbonate or phosphate.

After the respective one of the reactions ends, the reaction formulation may also be directly regenerated by adjusting a sulfuric acid titer of <1 wt.-% and the resulting solid matter may be filtered away.

The purity of the substances of the invention, i.e., the fraction of impurities accompanying the phenazinium compounds, can be determined analytically:

To identify and quantify in accordance with the invention the compounds contained in the substances, mass spectrometry is presently more specifically utilized, whereby the spectra can be measured more specifically under the following conditions: by means of electron spray ionization coupled with a quadrupole mass spectrometer (ESI/MS) or with a quadrupole ion trap (ESI/QIT-MS), Atmospheric Pressure Matrix Assisted Laser Desorption Ionization coupled with a quadrupole ion trap (AP-MALDI/QIT-MS) or Matrix Assisted Laser Desorption Ionization coupled with a time-of-flight mass spectrometer (MALDI-TOF). The MALDI-methods are preferred. To quantitatively determine the components in the substances, the sum of all the signals in the mass spectrum is set to 100 mole-%. The height of the individual signals detected is related thereto. It is thereby assumed that ionizability and sensitivity to the assignable molecule peaks are equally high.

Alternatively, the monomeric phenazinium compounds and the oligomeric phenazinium compounds contained as impurities in the substances may also be quantitatively determined by means of another method by which a mass spectrometer is coupled with a high-performance liquid chromatography unit (LC-MS-coupling) to associate the individual peaks in the HPLC chromatogram through the mass spectrum. After a first identification from a reference mixture by means of LC-MS-coupling, the quantitative determination may then also be carried out without LC-MS-coupling by using the retention times of the peaks for identification.

Alternatively, the HPLC method can also be used for quantitatively determining the monomeric phenazinium compounds and the small amounts of additionally contained oligomeric phenazinium compounds in the substances of the invention, the gel permeation chromatography being more specifically utilized. In this case, anionic ion-pairing wetting agents can be added to the mobile phase for enhanced separation of the positively charged compounds (ion-pair chromatography).

The method of the invention permits for example to prepare compounds of high purity and having the chemical formulae II, III, IV, and V already mentioned herein above.

The preparation method of the invention will be more fully understood from the following preparation examples:

Preparation Example 1

Without Addition of Another Halide 3-chloro-7-N,N-dimethylamino-2-methyl-5-phenyl-phenazinium chloride 1 g of 3-amino-7-N,N-dimethylamino-2-methyl-5-phenyl-phenazinium chloride was suspended in 15 ml of 35 wt.-% hydrochloric acid and heated to 50° C. Then, a saturated aqueous sodium nitrite solution (454 mg in 6 ml of water) was slowly added dropwise and was thereafter stirred for one hour at this temperature. The reaction formulation was cooled down to room temperature, the resulting black-blue solid matter was filtered away and dried. The yield was 615 mg (58.5% of the theory).

The purity of the resulting substance after quantitative analysis by means of mass spectrometry was found to be 94 mole-% i.e., 6 mole-% only of the substance utilized did not consist of the monomeric compound.

Preparation Example 2

With Addition of Another Halide 3-chloro-7-N,N-dimethylamino-2-methyl-5-phenyl-phenazinium chloride 1 g of 3-amino-7-N,N-dimethylamino-2-methyl-5-phenyl-phenazinium chloride was suspended in 15 ml of 35 wt.-% hydrochloric acid and heated to 50° C. Then, 347 mg of nickel(II) chloride were added and a saturated aqueous sodium nitrite solution (454 mg in 6 ml of water) was slowly added dropwise and was thereafter stirred for one hour at this temperature. The reaction formulation was cooled down to room temperature, the resulting black-blue solid matter was filtered away and dried. The yield was 724 mg (69.0% of the theory)

The purity of the resulting substance after quantitative analysis by means of mass spectrometry was found to be 90 mole-% i.e., 10 mole-% only of the substance utilized did not consist of the monomeric compound.

Preparation Example 3

With Addition of Another Halide 3-chloro-7-N,N-dimethylamino-2-methyl-5-phenyl-phenazinium chloride 1 g of 3-amino-7-N,N-dimethylamino-2-methyl-5-phenyl-phenazinium chloride was suspended in 15 ml of 35 wt.-% hydrochloric acid and heated to 50° C. Then, 271 mg of copper(I) chloride were added and a saturated aqueous sodium nitrite solution (454 mg in 6 ml of water) was slowly added dropwise and was thereafter stirred for one hour at this temperature. The reaction formulation was cooled down to room temperature, the resulting black-blue solid matter was filtered away and dried. The yield was 521 mg (49.5% of the theory).

The purity of the resulting substance after quantitative analysis by means of mass spectrometry was found to be 93 mole-% i.e., 7 mole-% only of the substance utilized did not consist of the monomeric compound.

Preparation Example 4

With Addition of Another Halide 3-bromo-7-N,N-dimethylamino-2-methyl-5-phenyl-phenazinium bromide 1 g of 3-amino-7-N,N-dimethylamino-2-methyl-5-phenyl-phenazinium chloride was suspended in 10 ml of 48 wt.-% hydrobromic acid and heated to 50° C. Then, 392 mg of copper(I) bromide were added and a saturated aqueous sodium nitrite solution (228 mg in 2 ml of water) was slowly added dropwise and was thereafter stirred for 30 minutes at this temperature. The reaction formulation was cooled down to room temperature, the resulting black-blue solid matter was filtered away and dried. The yield was 824 mg (64.0% of the theory).

The purity of the resulting substance after quantitative analysis by means of mass spectrometry was found to be even greater than 99 mole-% i.e., no impurities in the form of dimers and other oligomers could be evidenced in the substance utilized.

Preparation Example 5

Without Addition of Another Halide 3-bromo-7-N,N-diethylamino-5-phenyl-phenazinium bromide 3 g of 3-amino-7-N,N-diethylamino-5-phenyl-phenazinium chloride were suspended in 40 ml of 48 wt.-% hydrobromic acid and heated to 50° C. Then, an aqueous concentrated sodium nitrite solution (1.094 g in 10 ml of water) was slowly added dropwise over one hour and was thereafter stirred for another hour at this temperature. The reaction formulation was cooled down to room temperature and slowly incorporated in caustic soda lye. The resulting black-blue solid matter was filtered away and dried. The yield was 2.571 g (67.0% of the theory).

The purity of the resulting substance after quantitative analysis by means of mass spectrometry was found to be approximately 89 mole-% i.e., 11 mole-% only of the substance utilized did not consist of the monomeric compound.

Preparation Example 6

With Addition of a Pseudohalide 7-amino-2,8-dimethyl-3-thiocyanato-5-phenyl-phenazinium tetrafluoroborate 1 g of 3,7-diamino-2,8-dimethyl-5-phenyl-phenazinium chloride were suspended in 15 ml of 50 wt.-% tetrafluoroboric acid and heated to 50° C. Then, 10 ml of an aqueous solution consisting of 1.109 g sodium thiocyanate and 454 mg of sodium nitrite were added dropwise over one hour at a temperature of 50 to 60° C. and thereafter stirred for another hour at this temperature. The reaction formulation was cooled down to room temperature, the resulting black solid matter was filtered away and dried. The yield was 812 mg (64.0% of the theory).

The purity of the resulting substance after quantitative analysis by means of mass spectrometry was found to be approximately 90 mole-% i.e., 10 mole-% only of the substance utilized did not consist of the monomeric compound.

The thus obtained halogenated and pseudohalogenated phenazinium compounds in accordance with the present invention were added, alone or in combination with brighteners or wetting agents, to a copper electrolyte, more specifically to an acidic, preferably sulfuric acid bath.

To permit deposition of a copper layer onto a workpiece using an electrolytic method, said workpiece is brought, together with an anode, into contact with the bath. The bath contains copper ions and the halogenated and/or pseudohalogenated phenazinium compounds of the invention. For metal deposition, a flow of electric current is then generated between the workpiece and the anode.

The basic composition of the copper electrolyte may vary within wide limits. Generally, an acidic, copper ions containing aqueous solution of the following composition is used:

| | |
|---|---|
| copper sulfate ($CuSO_4 \cdot 5H_2O$) | 20-300 g/l |
| preferably | 180-220 g/l |
| sulfuric acid, conc. | 50-350 g/l |
| preferably | 50-90 g/l |
| chloride ions | 0.01-0.25 g/l |
| preferably | 0.05-0.14 g/l |

Instead of the copper sulfate, it is also at least partially possible to use other copper salts. The sulfuric acid as well may be replaced in part or in whole with fluoroboric acid, methane sulfonic acid or other acids. The chloride ions are added as alkali chloride (e.g., sodium chloride) or in the form of hydrochloric acid reagent grade. The addition of sodium chloride can be dispensed with in part or in whole if the added substances already contain halide ions.

The phenazinium compounds of the present invention are preferably added to the bath in a concentration of from 0.00005-0.1 g/l.

The bath may moreover contain current brighteners, levellers or wetting agents. In order to obtain bright copper deposits exhibiting predetermined physical properties, at least one water-soluble sulfur compound and one oxygen-containing, high molecular compound may be added to the acidic bath of the invention. Further additives such as nitrogen-containing sulfur compounds and/or polymeric nitrogen compounds may also be used. The oxygen-containing high molecular compounds more specifically are glycol ethers of alkyl phenols, alkanols, and alkane diols, further glycol esters of aliphatic carbonic acids as well as polyethers and polyalcohols.

The individual components are contained in the ready-to-use bath in the following limit concentrations:

| current oxygen-containing | |
|---|---|
| high molecular compounds | 0.005-20 g/l |
| preferably | 0.01-5 g/l |
| current water-soluble organic | |

-continued

| | |
|---|---|
| sulfur compounds | 0.0005-0.4 g/l |
| preferably | 0.001-0.15 g/l |

Table 1 lists some of the utilizable oxygen-containing high molecular compounds.

Some sulfur compounds are set forth in Table 2. Suited functional groups are incorporated for water solubility.

Sulfur-containing nitrogen compounds, more specifically nitrogen-containing thio compounds, preferably thiourea derivatives and/or polymeric nitrogen compounds such as polyamines and polyamides, may be utilized in the following concentrations:

| | |
|---|---|
| | 0.0001-0.50 g/l |
| preferably | 0.0005-0.04 g/l |

Preferred nitrogen-containing thio compounds are set forth in Table 3 and preferred polymeric nitrogen compounds in Table 4.

For preparing the bath, the individual components are added to the basic composition. The operating conditions for the bath may more specifically be adjusted as follows:

| | |
|---|---|
| pH-value: | <1 |
| temperature: | 15° C.-50° C., preferably 20° C.-40° C. |
| cathodic current density: | 0.5-12 A/dm$^2$, preferably 3-7 A/dm$^2$ |

The electrolyte may be agitated through a strong incident flow and possibly by injecting clean air so that the surface of the electrolyte is strongly agitated. This maximizes the mass transfer in the proximity to the electrode and allows the highest possible current densities. The movement of the cathodes also promotes mass transfer at the respective one of the surfaces. Increased convection and movement of the electrodes permit to achieve constant, diffusion-controlled deposition. The movements may be horizontal, vertical and/or caused by vibrations. In combination with air injection, they are particularly efficient.

Copper may be electrochemically replenished by dissolving copper anodes in order to keep the copper content constant. The copper used for the anodes may be a copper containing 0.02 to 0.07 wt.-% phosphorus. The copper anodes should be enclosed in a filter bag. The use of inert anodes made of platinized titanium or other coatings is also possible. Present day's prior art lines are lines in which the workpiece is coated in a vertical or horizontal position.

At need, filters for retaining mechanical and/or chemical residues may be inserted into the electrolyte circuits.

The copper electrolyte of the invention is perfectly suited for producing a decorative deposit. It may furthermore be utilized to electrolytically fill blind microvias in printed circuit boards. This constitutes a future-oriented technology for manufacturing chip carriers in particular since, in thin circuit traces, increased reliability is achieved over the technique using copper sleeves. In a similar way, the copper electrolyte of the invention provides an elegant solution to produce circuit structures onto semiconductor substrate surfaces (wafers) provided with recesses during the manufacturing of integrated circuits. Using the copper plating method of the invention, an almost constant layer thickness (planarity) is achieved over the entire surface of the wafer, independent of the recesses having a high aspect ratio (1:10), so that such recesses are filled with copper.

The invention will be understood better upon reading the following method examples.

Method Example 1

Comparative Example

In an electrolytic cell with soluble, phosphorus-containing copper anodes, a copper bath having the following composition was utilized:
200 g/l of copper sulfate ($CuSO_{4.5}H_2O$)
60 g/l of sulfuric acid, conc.
0.12 g/l of sodium chloride
The following brighteners were added:
1.5 g/l of polypropylene glycol (800 Da (dalton)),
0.006 g/l of 3-mercapto-propane-1-sulfonic acid, sodium salt At an electrolyte temperature of 25° C. and at a current density of 4 A/dm$^2$, a uniform, bright, slightly hazy deposit was obtained on a brushed brass sheet.

Method Example 2

Comparative Example 4 mg/l of 7-dimethylamino-3-chloro-5-phenyl-phenazinium chloride (prepared according to the instructions given in JP 60-056086 A) were further added to the electrolyte according to method example 1. A quantitative analysis of this substance by means of mass spectrometry evidenced a fraction of impurities (more specifically of dimers and trimers of this compound) of approximately 43 mole-%.

After copper had been deposited under the conditions indicated in method example 1, the copper layer obtained had a slightly improved appearance. In this case, the brass sheet had a brighter appearance but showed burns (copper powder deposit) at the edges because of the high current density occurring there.

Method Example 3

Example in Accordance with the Invention 4 mg/l of the compound of the invention 3-chloro-7-N,N-dimethylamino-2-methyl-5-phenyl-phenazinium chloride were further added to the electrolyte in accordance with method example 1.

After copper had been deposited under the conditions indicated in method example 1, the copper layer obtained on the brass sheet had a very good appearance. The deposit was mirror bright and did not show any burns. The brush lines were totally invisible now. This was indicative of an excellent leveling effect of the copper electrolyte.

Method Example 4

Example in Accordance with the Invention

Only 3 mg/l of the compound of the invention 7-amino-2,8-dimethyl-3-thiocyanato-5-phenyl-phenazinium-tetrafluoroborate were further added to the electrolyte in accordance with method example 1.

After copper had been deposited under the conditions indicated in example 1, the brass sheet had an extremely good appearance. The deposit was extremely brilliant and mirror-like. The sheet showed no burns. The brush lines were absolutely invisible. This was indicative of an excellent leveling effect of the copper electrolyte although the quantity of mixture had been reduced.

Result of the examples 1 through 4: it could be shown that without the halogenated or pseudohalogenated monomeric phenazinium compounds of the invention but a low leveling effect could be achieved. It could also be shown that the preparation method has a decisive influence on the quality of the halogenated and pseudohalogenated compounds used. The chlorinated compounds prepared using the method in accordance with JP 60-056086 A could not contribute to form copper layers of a satisfactory quality. The halogenated and pseudohalogenated monomeric phenazinium compounds, by contrast, have a good effect. The utilized concentration could be clearly reduced over conventional additives with an excellent result being still achieved.

Method Example 5

Comparative Test

To coat a printed circuit board having blind microvias, a copper bath of the following composition was utilized in an electrolytic cell having soluble, phosphorus containing copper anodes:

150 g/l of copper sulfate ($CuSO_{4.5}H_2O$)
200 g/l of sulfuric acid, conc.
0.05 g/l of sodium chloride
The following brighteners were added:
0.5 g/l of polypropylene glycol (820 Da),
0.005 g/l of bis-(ω-sulfopropyl)-disulfide, disodium salt At an electrolyte temperature of 25° C. and at a current density of 1 A/dm², a slightly hazy deposit was obtained on a previously 8 μm copper-reinforced printed circuit board having small blind holes (blind microvias) after an exposure time of 114 minutes, with a blind hole of a width of 110 μm and a depth of 60 μm being hardly filled with copper.

Method Example 6

Example in Accordance with the Invention 4 mg/l of the compound of the invention, 3-bromo-7-N,N-diethylamino-5-phenyl-phenazinium bromide, were additionally added to the electrolyte according to method example 5. After copper had been deposited under the conditions indicated in method example 5, the appearance of the printed circuit board could be improved. The blind vias of a width of 110 μm and a depth of 60 μm were completely and selectively filled with copper. After copper plating had been performed, there was hardly any visible well on the copper surface. The overall quantity of deposited copper was low.

This result is a great improvement over the prior art technique known to be used for electrolytic copper plating of blind vias since these may be filled in a much better way. The reason therefore is the substantially improved leveling effect of the copper plating bath obtained by the phenazinium compound of the invention. Further, the reliability of the bond between the copper deposited onto the wall of a blind via and the copper layer exposed in the hole is much better than using the conventional copper plating technique. For, using the compounds in accordance with the invention, no delaminations could be detected between the two metal layers during a thermal solder shock test, whereas there is a risk that the use of known comparable additives induces such delaminations under these conditions.

It is understood that the examples and embodiments described herein are for illustrative purpose only and that various modifications and changes in light thereof as well as combinations of features described in this application will be suggested to persons skilled in the art and are to be included within the spirit and purview of the described invention and within the scope of the appended claims. All publications, patents and patent applications cited herein are hereby incorporated by reference.

TABLE 1

| Oxygen containing high molecular compounds |
|---|
| Carboxy methyl cellulose |
| Nonyl phenol-polyglycol ether |
| Octane diol-bis-(polyalkylene glycol ether) |
| Octanol polyalkylene glycol ether |
| Oleic acid polyglycol ester |
| Polyethylene glycol-polypropylene glycol (block or copolymerisate) |
| Polyethylene glycol |
| Polyethylene glycol-dimethyl ether |
| Polypropylene glycol |
| Polyvinyl alcohol |
| β-naphthol-polyglycol ether |
| Stearic acid polyglycol ester |
| Stearyl alcohol polyglycol ether |

TABLE 2

| sulfur compounds |
|---|
| 3-(benzthiazolyl-2-thio)-propyl sulfonic acid, sodium salt |
| 3-mercapto propane-1-sulfonic acid, sodium salt |
| Ethylene dithio dipropyl sulfonic acid, sodium salt |
| Bis-(p-sulfophenyl)-disulfide, disodium salt |
| Bis-(ω-sulfobutyl)-disulfide, disodium salt |
| Bis-(ω-sulfo hydroxy propyl)-disulfide, disodium salt |
| Bis-(ω-sulfopropyl)-disulfide, disodium salt |
| Bis-(ω-sulfopropyl)-sulfide, disodium salt |
| Methyl-(ω-sulfopropyl)-disulfide, disodium salt |
| Methyl-(ω-sulfopropyl)-trisulfide, disodium salt |
| O-ethyl-dithio carbonic acid-S-(ω-sulfopropyl)-ester, potassium salt |
| Thioglycolic acid |
| Thiophosphoric acid-O-ethyl-bis-(ω-sulfopropyl)-ester, disodium salt |
| Thiophosphoric acid-tris-(ω-sulfopropyl)-ester, trisodium salt |

TABLE 3

| nitrogen containing thio compounds: |
|---|
| N-acetyl thiourea |
| N-trifluoroacetyl thiourea |
| N-ethyl thiourea |
| N-cyanoacetyl thiourea |
| N-allyl thiourea |
| o-tolyl thiourea |
| N,N'-butylene thiourea |
| Thiazolidine thiol(2) |
| 4-thiazoline thiol(2) |
| Imidazolidine(2) (N,N'-ethylene thiourea) |
| 4-methyl-2-pyrimidine thiol |
| 2-thiouracil |
| Saccharine, sodium salt |

TABLE 4

| polymeric nitrogen compounds |
| --- |
| Polyethylene imine |
| Polyethylene imide |
| Polyacylic acid amide |
| Polypropylene imine |
| Polybutylene imine |
| N-methyl polyethylene imine |
| N-acetyl polyethylene imine |
| N-butyl polyethylene imine |

The invention claimed is:

1. Pseudohalogenated monomeric phenazinium compounds of a purity of at least 85 mole-% having the following chemical formula I:

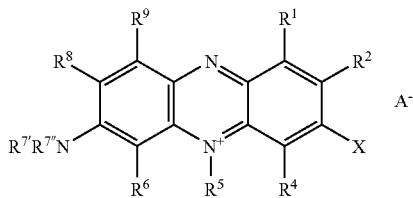

wherein $R^1$, $R^2$, $R^4$, $R^6$, $R^{7'}$, $R^{7''}$, $R^8$ and $R^9$ are selected independently of each other from a group consisting of hydrogen, halogen, amino, aminoalkyl, hydroxy, cyano, thiocyanate, isothiocyanate, cyanate, isocyanate, lower alkyl, unsubstituted aryl, and substituted aryl wherein the substituents are selected from the group consisting of alkyl, halogen, hydroxyl, amino, wherein amino is $NH_2$, NHR or NR'R", wherein R, R' and R" are lower alkyl, cyano, thiocyanate and mercapto, $R^5$ is selected from a group consisting of lower alkyl, unsubstituted aryl and substituted aryl wherein the substituents are selected from the group consisting of alkyl, halogen, hydroxyl, amino, wherein amino is $NH_2$, NHR or NR'R", wherein R, R' and R" are lower alkyl, cyano, thiocyanate and mercapto, X is a pseudohalogen and $A^-$ is an acid anion selected from the group consisting of sulfate, hydrogen sulfate, halide, tetrafluoroborate, hexafluorophosphate, nitrate, acetate, trifluoroacetate and methanesulfonate.

2. The phenazinium compounds according to claim 1, characterized in that $R^1$, $R^2$, $R^4$, $R^6$, $R^{7'}$, $R^{7''}$, $R^8$ and $R^9$ are selected independently of each other from a group consisting of hydrogen and lower alkyl.

3. The phenazinium compounds according to claim 2, characterized in that lower alkyl is methyl or ethyl.

4. The phenazinium compounds according to claim 1, characterized in that $R^5$ is aryl.

5. The phenazinium compounds according to claim 4, characterized in that aryl is phenyl.

6. The phenazinium compounds according to claim 1, characterized in that X is thiocyanate.

7. The phenazinium compounds according to claim 1, characterized in that they are selected from a group consisting of 7-amino-2,8-dimethyl-3-thiocyanato-5-phenyl-phenazinium salt.

8. The phenazinium compounds according to claim 7, characterized in that the salt is selected from a group consisting of hydrogen sulfate and tetrafluoroborate.

9. The phenazinium compounds according to claim 7, characterized in that they are selected from a group consisting of 7-amino-2,8-dimethyl-3-thiocyanato-5-phenyl-phenaziniumtetraffluoroborate.

10. The phenazinium compounds according to claim 2, characterized in that $R^5$ is aryl.

11. The phenazinium compounds according to claim 3, characterized in that $R^5$ is aryl.

12. The phenazinium compounds according to claim 5, characterized in that X is thiocyanate.

* * * * *